(12) United States Patent
Kjelleberg et al.

(10) Patent No.: US 6,555,356 B2
(45) Date of Patent: *Apr. 29, 2003

(54) METHODS FOR MICROBIAL REGULATION

(75) Inventors: Staffan Kjelleberg, La Perouse (AU); Peter David Steinberg, Newtown (AU); Peter Canisius De Nys, Bronte (AU); Ria Maximilien, Coogee (AU); Michael Manefield, Bondi Beach (AU); Michael Givskov, Copenhagen (DK); Lone Gram, Hellerup (DK)

(73) Assignee: Unisearch Limited, Kensington (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/913,762
(22) PCT Filed: Mar. 25, 1996
(86) PCT No.: PCT/AU96/00167
§ 371 (c)(1),
(2), (4) Date: Mar. 4, 1998
(87) PCT Pub. No.: WO96/29392
PCT Pub. Date: Sep. 26, 1996

(65) Prior Publication Data
US 2002/0037578 A1 Mar. 28, 2002

(30) Foreign Application Priority Data
Mar. 23, 1995 (AU) .............................. PN1912

(51) Int. Cl.[7] .................................................. C12N 1/38
(52) U.S. Cl. .................. 435/244; 424/58; 514/473; 435/170; 435/171
(58) Field of Search ........................... 424/58; 514/473; 435/244, 170, 171

(56) References Cited

U.S. PATENT DOCUMENTS

| | | | |
|---|---|---|---|
| 5,196,318 A | 3/1993 | Baldwin et al. | 435/69.1 |
| 5,591,872 A | 1/1997 | Pearson et al. | 549/321 |
| 5,989,323 A | * 11/1999 | Taylor | 106/15.05 |
| 6,057,288 A | 5/2000 | Pearson et al. | 514/2 |
| 6,060,046 A | * 5/2000 | Steinberg et al. | 424/78.09 |

FOREIGN PATENT DOCUMENTS

WO    WO 96/01294    1/1996

OTHER PUBLICATIONS

Ochi, Antimicrobial consitutents [of marine algae], Suisangaku Shiriizu (1983), 45 (Kaiso no Seikagaku to Riyo), 101–119.*

(List continued on next page.)

*Primary Examiner*—Irene Marx
(74) *Attorney, Agent, or Firm*—Morgan, Lewis & Bockius LLP

(57) ABSTRACT

A method and microbial culture medium for inhibiting homoserine lactone and/or acylated homoserine lactone regulated processes in microorganisms using furanone compounds.

42 Claims, 6 Drawing Sheets

OTHER PUBLICATIONS de Nys et al., Broad Spectrum Effects of Secondary Metabolites from the Red Alga Delisea Pulchra in Antifouling Assays, Biofouling 8 : 259–71 (1995).*

Reichelt et al., "Antimicrobial activity from marine algae: Results of a large–scale screening programme", Hydrobiologia, vol. 116/117, pp. 158–168, 1984.

Huisman et al., "Sensing Starvation: A Homoserine Lactone–Dependent Signaling Pathway in *Escherichia coli*" Science, vol. 265, pp. 537–539, Jul. 22, 1994.

Beecham, C.M. et al., "The first synthesis of fimbrolides, a novel class of halogenated lactones naturally occuring in the red seaweed *Delisia fimbriata* (Bonnemaisoniaceae)", *Tetrahedron Letters*, No. 19, 1979, pp. 1649–1652.

deNys, R. et al., "New halogenated furanons from the marine alga *Delisea pulchra* (cf. Fimbriata)"; *Tetrahedron*, vol. 49, 1993, pp. 11213–11220.

Kazlouskas, R. et al., "A new class of halogenated lactones from the red alga *Delisea Fimbrata* (Bonnemaisoniaceae"; *Tetrahedron Letters*, No. 1, 1977, pp. 37–40.

Ohta, Keiichi, "Antimicrobial compounds in the marine red alga *Beckerella subcostatum*"; *Agricultural and Biological Chemistry*; vol. 41, No. 10, 1977, pp. 2105–2106.

* cited by examiner

| R1 | R2 | R3 |
|----|----|----|
| H | Br | Br |
| H | H | Br |
| H | Br | H |
| H | H | Cl |
| H | Cl | H |
| H | H | I |
| H | I | H |
| H | Cl | Cl |
| H | I | I |
| H | H | H |
| OH | Br | Br |
| OH | H | Br |
| OH | Br | H |
| OH | H | Cl |
| OH | Cl | H |
| OH | H | I |
| OH | I | H |
| OH | Cl | Cl |
| OH | I | I |
| OH | H | H |
| OAc | Br | Br |
| OAc | H | Br |
| OAc | Br | H |
| OAc | H | Cl |
| OAc | Cl | H |
| OAc | H | I |
| OAc | I | H |
| OAc | Cl | Cl |
| OAc | I | I |
| OAc | H | H |

| | R1 | R2 | R3 | R4 |
|---|---|---|---|---|
| 1 | H | Br | Br | Br |
| 2 | H | Br | H | Br |
| 3 | OAc | Br | H | Br |
| 4 | OH | Br | H | Br |
| 5 | OAc | Br | H | I |
| 8 | H | H | Br | Br |
| 10 | OAc | Br | Br | Br |

| | R1 | R2 | R3 | R4 |
|---|---|---|---|---|
| 12 | H | Br | H | Br |
| 13 | H | H | Br | Br |

| | R1 | R2 | R3 | R4 |
|---|---|---|---|---|
| 14 | H | H | Br | Br |

| | R1 | R2 | R3 | R4 |
|---|---|---|---|---|
| 15 | H | Br | Br | Br |
| 16 | H | Br | H | Br |
| 17 | H | H | Br | Br |

METHODS FOR MICROBIAL REGULATION

BACKGROUND OF THE INVENTION

This application was filed under 35 USC 371 as the national phase of PCT/AU96/00167, Mar. 25, 1996.

TECHNICAL FIELD

The present invention relates to methods for regulating processes of microorganisms. In particular, methods and culture media including furanones for inhibiting homoserine lactone (HSL) and/or acylated homoserine lactone (AHL) regulated processes in microorganisms.

DESCRIPTION OF THE RELATED ART

Microorganisms, including bacteria, fungi and algae, have a profound effect upon the activities of humans and animals. Considerable efforts have been made to find compounds and methods for the control of such micro organisms. There is a need to continually find new compounds and methods for this purpose is due, in part at least, to the capacity of such microorganisms to rapidly mutate to circumvent the compounds and methods already developed.

One set of fundamental regulator agents which are widespread in bacteria, including human pathogens, are known as homoserine lactones (HSL) or acylated homoserine lactones (AHL). The AHL regulatory systems in bacteria are two component regulatory systems which regulate intercellular activity in response to environmental conditions and extracellular signal molecules. This system was first discovered in the bioluminescent marine bacteria *Vibrio harveyi* and *V. fischeri* where it is used to control expression of bioluminescence. In principle, the system is comprised of two proteins—LuxR and LuxI. The LuxI enzyme is encoded by a luxI gene and produces a related family of signal molecules known as the homoserine lactones. These signal molecules bind to the LuxR regulator which is then activated and serves both as a positive regulator for the structural genes which encode the enzymes responsible for bioluminescence, and as a positive regulator for the luxI gene itself. The entire system is amplified via a process of auto induction. Additional molecules serve as regulators of the LuxR-LuxI system.

While initially discovered for bioluminescent bacteria, this regulatory system has now been found in numerous other microorganisms, and is involved in a wide variety of bacterial activities (Swift et al. 1994. Fuqua et al. 1994). These activities include, but are not restricted to, exoenzyme production in the plant pathogen *Erwinia carotovora* and in *Pseudomonas aeruginosa*, the causative agent of cystic fibrosis, and Ti plasmid transfer from *Agrobacterium tumefaciens* to plants. In all instances, acylated homoserine lactone, or homoserine lactone-like compounds are the regulatory auto inducers.

Since these regulatory systems are widespread among bacteria, and because they control processes leading to bacterial invasion of host organisms, it is likely that other organisms will have evolved defence mechanisms against these systems. So far none have been found. The present inventors have now developed methods of inhibiting microbial processes using compounds that are mimics of the homoserine lactone family of regulatory compounds.

SUMMARY OF THE INVENTION

In a first aspect, the present invention consists of a method of inhibiting a homoserine lactone and/or acylated homoserine lactone—regulated process in a microorganism comprising exposing the microorganism to a furanone compound so as to inhibit the process.

In a second aspect, the present invention consists of a microbial culture medium for inhibiting a homoserine lactone and/or acylated homoserine lactone—regulated process in a microorganism, the medium comprising growth and/or maintenance ingredients and a furanone compound.

DETAILED DESCRIPTION

Accordingly, in a first aspect the present invention consists in a method of inhibiting an homoserine lactone (HSL) and/or acylated homoserine lactone (AHL) regulated process in a microorganism comprising exposing the microorganism to a furanone compound so as to inhibit the process.

Figure 3:
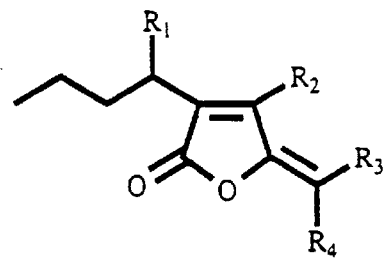
FIG. 3 shows the structure of furanones tested (compounds 1–5, 8, 10 and 12–16 in assays.
Figure 3:
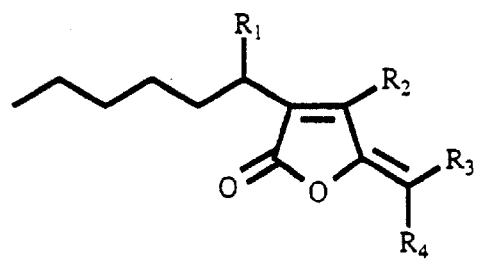
Figure 3:
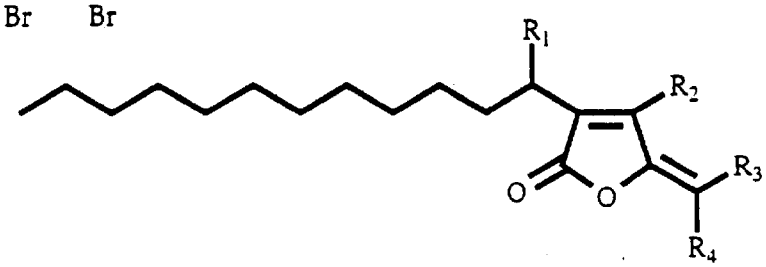
Figure 3:
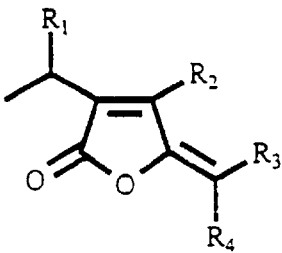

In a preferred form, the furanone compound is derived from the alga *Delisea pulchra* or chemical modifications or derivatives thereof. More preferably the furanone compound is selected from the group consisting of the compounds of Formula 1 and Formula 2 and even more preferably, the furanone compound is selected from the group consisting of the compounds of FIG. 3.

The furanone compounds are typically used at a concentration greater than 10 ng/ml. Preferably the furanone compounds are used at concentration from 100 ng to 1 mg/ml and more preferably used at a concentration from 1 µg to 100 µg/ml.

The HSL and AHL regulated processes that can be inhibited by the present invention include motility, swarming, swimming, exoenzyme production, indigo formation, adhesion, attachment and luminescence. It will be appreciated by persons skilled in the art, however, that other AHL and/or HSL regulated processes could also inhibited by the methods of the present invention.

In order to inhibit the motility or swarming of microorganisms when cultured in vitro, the furanones used in the present invention can be included in culture media so that when the motile microorganisms are grown in or on the media their motility or swarming processes are inhibited. This has particular utility when mixed cultures of microorganisms are cultured on semi-solid agar culture plates where there is a problem of one motile microorganism swarming over the plate and preventing the isolation or selection of other non-motile microorganisms present in the mixture. The incorporation of one or more of the furanones in a culture medium would inhibit the motility or swarming processes regulated by HSL and/or AHL of any microorganisms cultured thereon.

The method of the present invention is applicable for inhibiting processes in microbial pahtogens of plants, animals and humans in vivo. Typical plant pathogens include *Serratia liquifaciens* and *Erwinia carotovora*, animal pathogens include *Vibrio harveyi* and *Vibrio anguillarum* and human pathogens include *Pseudomonas aeruginosa* and *Proteus mirabilis*.

It will be appreciated that the methods of the present invention can be carried out on microorganims by treating them directly with furanones as well as indirectly by, for example, giving or applying furanones to plants, animals or humans so as to inhibit HSL and/or AHL regulated processes of the microorganisms of interest in or on the plants, animals or humans. The effect of the furanones will be the reduction or inhibition of the regulated process of interest, irrespective of specific action on the HSL and/or AHL pathway itself.

In a second aspect, the present invention consists in a microbial culture medium for inhibiting an homoserine lactone (HSL) and/or acylated homoserine lactone (AHL) regulated process in a microorganism, the medium comprising growth and/or maintenance ingredients and a furanone compound.

In a preferred form, the furanone compound is derived from the alga *Delisea pulchra* or chemical modifications or derivatives thereof. More preferably the furanone compound is selected from the group consisting of the compounds of Formula 1 and Formula 2 and even more preferably, the furanone compound is selected from the group consisting of the compounds of FIG. 3.

The furanone compound is typically included in the medium to give a final concentration in use of greater than 10 ng/ml. Preferably the furanone compound has a final concentration from 100 ng to 1 mg/ml and more preferably the furanone compound has a final concentration from 1 $\mu$g to 100 $\mu$g/ml.

Figure 1:
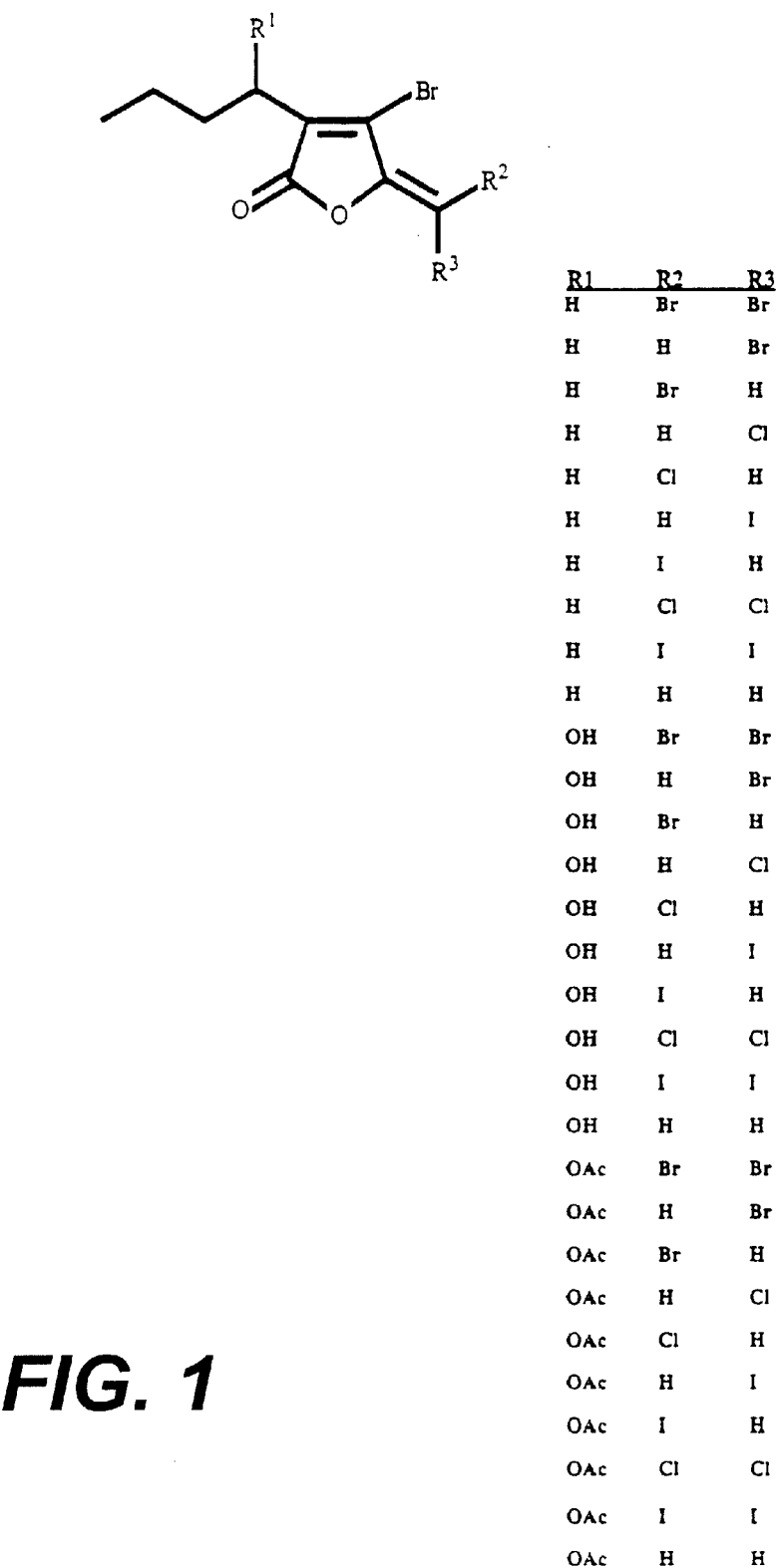
FIG. 1 shows the structure of furanones from *Delisea pulchra* Formula 1.

As used herein the term 'a compound of Formula 1' means a compound being a furanone of the structure shown in FIG. 1, wherein $R_1$ is a hydrogen atom, a hydroxyl, ester or an ether group and wherein $R_2$ and $R_3$ are each a hydrogen atom or a halogen atom.

Figure 2:
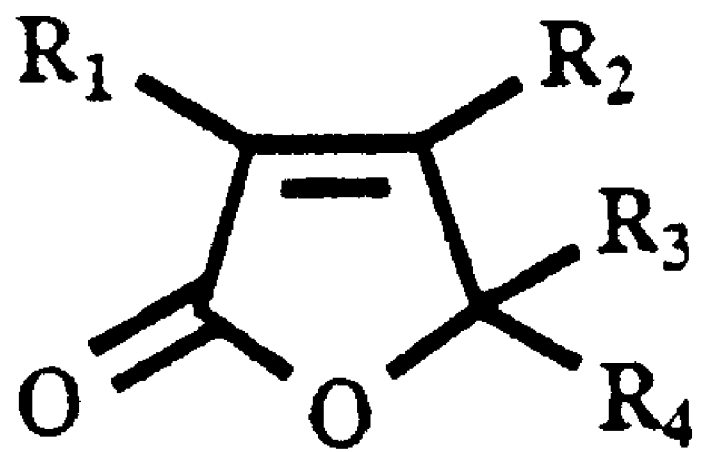
FIG. 2 shows the structure of furanones from *Delisea pulchra*, Formula 2. R1, R2, R3 and R4 are each a hydrogen, halogen, methyl, alkyl, hydroxyl, ether or ester group, or combinations of these groups.

As used herein the term 'a compound of Formula 2' means a compound being a furanone of the structure shown in FIG. 2 wherein $R_1$, $R_2$, $R_3$ and $R_4$ are each a hydrogen, halogen, methyl, alkyl, hydroxyl, ether or ester group, or combinations of these groups.

The compounds used in the present invention consist of a series of structurally related furanones. Some of these compounds (FIG. 1) have been previously described in the literature, in part by the present inventors (Kazlauskas et al., 1977; de Nys et al., 1992: de Nys et al., 1993), where their molecular structures have been elucidated and characterised by nuclear magnetic spectroscopy, mass spectrometer, ultraviolet and infra-red spectroscopy and optical rotation ( D). The compounds all share a basic carbon skeleton consisting of a furanone moiety with an alkyl side chain at the 3-position of the basic structure. The substitution of hydrogen, hydroxy and acetoxy groups at the $R_1$ position, and hydrogen, bromine, chlorine and iodine at the $R_2$, $R_3$ position is preferred and results in a large series of structurally related metabolites (FIG. 1). The combination of the most feasible substitutions at these positions results in 30 possible structures, of which 13 have been characterised. In addition, the present inventors have now tested several synthetic analogues of these compounds (FIGS. 2 and 3), which, while sharing the basic furanone skeleton, differ in the length of their alkyl side chains. The present invention is intended to cover inter alia, the use of all of the 30 compounds in FIG. 1, as well as the extension of these structures shown in FIGS. 2 and 3.

The furanone compounds are close structural analogues of the AHL family of regulators (the structure of homoserine lactone and related regulatory molecules are described in Swift et al. 1994, and Fuqua et al. 1994), and it now seems that these compounds are in fact mimics of the homoserine lactone family of regulatory compounds. Thus the furanones are likely to be broadly useful as competitive inhibitors of these regulatory systems in a wide variety of applications.

EXAMPLES

Methods

For the tests described below, *Delisea pulchra* metabolites (furanone compounds) were extracted as follows: The alga was collected from Cape Banks, NSW, Australia and frozen on collection. The tissue was subsequently freeze dried, extracted with dichloromethane, and the crude extract reduced in vacuo. Purified metabolites were isolated by vacuum liquid chromatography followed by high performance liquid chromatography (de Nys et al., 1993). The structural elucidation of purified metabolites was carried out using a combination of nuclear magnetic resonance spectroscopy and mass-spectrometry techniques. Previously characterised Delisea metabolites and synthetic analogues set out in FIG. 3 were used in biological testing.

The furanone compounds and their analogous were tested against microorganisms as outlined below. All tests (bioassays) were done in the laboratory under controlled conditions.

Inhibition of homoserine lactone mediated systems in bacteria: swarming, exoenzyme, indigo production, and bioluminescence All bacteria were precultured in liquid LB medium or on LB plates at room temperature.

*Serratia liquefaciens* (Swarming and Exoprotease) Assay

*Serratia liquefaciens* was grown in liquid LB medium at room temperature to an optical density of 0.3 at 450 nm and stable inoculated onto LB agar (0.7% agar) plates. Plates were incubated at 30° C. and observed regularly for swarming behaviour. The effect on swarming of furanone compounds was tested by adding (after sterilisation and cooling of the agar) compounds 1–13 (FIG. 3). in the concentration range of 5–100 $\mu$g/ml, to the plates.

For assays of production of exoproteases by *Serratia liquifaciens* the bacteria were cultured as above and inoculated in liquid LB medium. The effects of furanone compounds were tested by adding compounds 3 and 4 (FIG. 3) at 100 $\mu$g/ml. Aliquots were withdrawn from the cultures, centrifuged and sterile filtered. Sixty microliters of supernatant were added to wells in skim milk agar plates (1.5% skim milk in M9 medium). Plates were incubated at room temperature and observed for clearing zones around the wells.

The effect on growth of *Serratia liquefaciens* by furanone compounds was also measured in liquid LB medium by comparing growth of cultures without the addition of compounds versus growth of cultures with added furanone compounds (100 $\mu$g/ml of compounds 1–13 (FIG. 3) in separate cultures). Growth was measured as optical density at 450 nm and followed over a 48 hr period.

*Chromobacterium violencia* (Indigo) Assay

A mutant of *Chromobacterium violencia* negative for the HSL auto inducer was used in the assay. The strain was pour plated in LB medium at high density and wells were punched after the media had set. Sterile, filtered supernatants from various HSL producing strains were added to the wells. Plates were incubated at 30° C. and observed for the formation of purple zones (due to indigo production) around the wells. The effects of furanone compounds 1 and 2 (FIG. 3) were assessed by running this assay on plates of LB medium containing furanone compounds at a concentration of 100 μg/ml. The effects of the compounds on growth of Chromobacterium were assessed as above.

Pseudomonas aeruginosa (Elastase) Assay

Inoculants from precultures were streaked onto Peptone-Tryptic Soy Broth agar containing 0.3% elastin. Plates were incubated at 37° C. and observed for hydrolysis of the elastin. The effect of furanone compounds was assess by adding compounds 1–4 (100 μg/ml) to the plates and comparing zones of hydrolysis in plates with and without the compounds.

Erwinia carotovora (Exoenzyme) Assay

Inoculants from precultured E. carotovora were added to slices of potatoes. Degradation (softening and browning) of the potato was compared on slices with and without furanone compounds (3 and 4).

Vibrio fisheri and V. harveyi (Bioluminescence) Assays

Initial assays for both strains of Vibrio were streaked onto LB agar plates (with 2% NaCl) with and without furanone compounds 1–4 at 5–100 μg/ml. Bioluminescence of the plates was visually assessed after 24 hours of incubation at room temperature. In subsequent assays, both strains were grown in liquid culture in the presence of furanones. Bioluminescence was assayed via a luminometer. The effects of furanones on growth of both strains were assayed as above.

Inhibition of Surface Motility and Adhesion

As well as specifically affecting well defined AHL mediated bacterial characteristics, furanones also inhibit other bacterial properties, in particular surface motility and adhesion. Like their interference with other AHL systems furanones interfere with or inhibit surface motility and swarming without necessarily having general growth inhibitory or microbiocidal effects. Proteus mirabilis and several characterised (but not yet taxonomically identified) marine isolates were used in these tests.

Proteus mirabilis and Marine Isolates (Swarming Assay)

Methods followed those described for Serratia liquefaciens (above). Inhibition of growth of these bacteria by furanones was assessed as above.

Marine Isolates (Adhesion Assays)

Six marine bacterial strains from submerged surfaces on the coast near Sydney were isolated and cultured as above in LB medium (with 2% NaCl). Attachment assays were done in two ways. Firstly, furanones were coated onto plastic dishes at several concentrations, and the dishes attached to frames. Each frame was placed in media which contained $10^7$/ml of one or the 6 bacterial isolates. After 2 hours, the frames were removed, rinsed thoroughly, stained with DAPI, and the number of attached bacteria on each dish via epifluorescence microscopy.

Secondly, inhibition of attachment was tested by pre-incubating the strains with furanones, so that the cells could take up the compounds. Three pre-incubation periods were used; 1/2, 3 and 10 hours. At the end of the pre-incubation period, the cells were washed, placed into experimental containers at $10^7$/ml, and plastic dishes (uncoated) placed into the containers. After 2 hours the frames with the dishes were removed, rinsed, and the number of attached cells counted as above.

Inhibition of Growth of Bacteria and Fungi by Compounds of Formula 2

In addition to the tests described above, the effects of selected compounds of the general formula 2 on growth of bacteria, one yeast (Candida albicans) and one fungus (Helminthosporium sp.) were assessed. Bacteria were grown in liquid media in the presence of different concentrations of furanones and growth measured via changes in optical density (OD). Fungal assays were done by inoculating agar plates with spores. These plates contained different concentrations of furanone compounds in wells within the plates. Zones of inhibition around these wells were measured after 48 hours.

RESULTS OF BIOASSAYS

Effects on AHL Mediated Processes

Figure 4A:
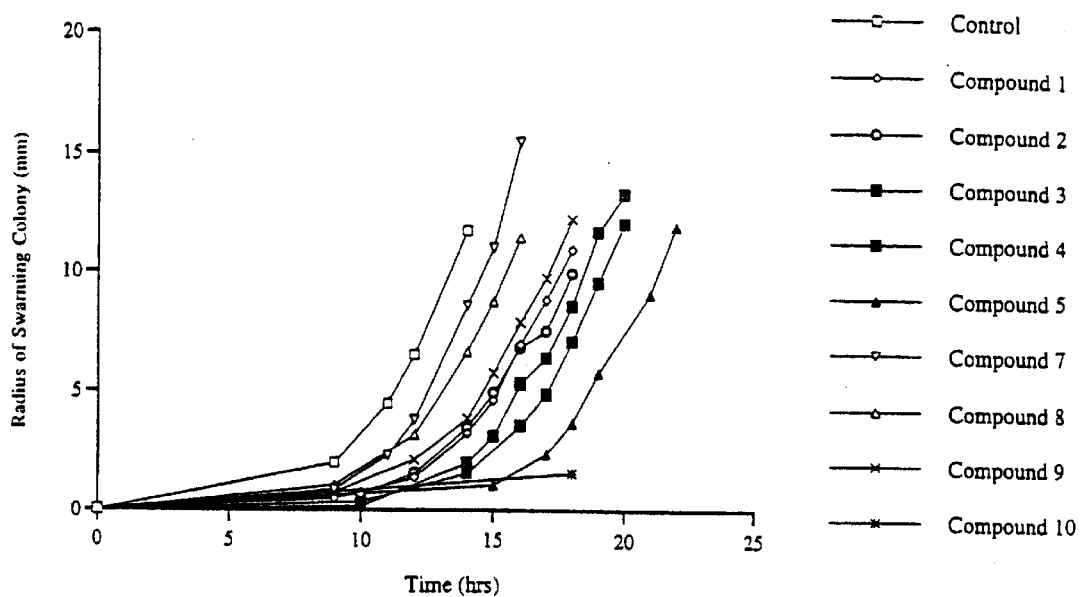
FIG. 4 shows the inhibition of AHL-regulated swarming in *Serratia liquifaciens* by furanones.
Figure 4B:
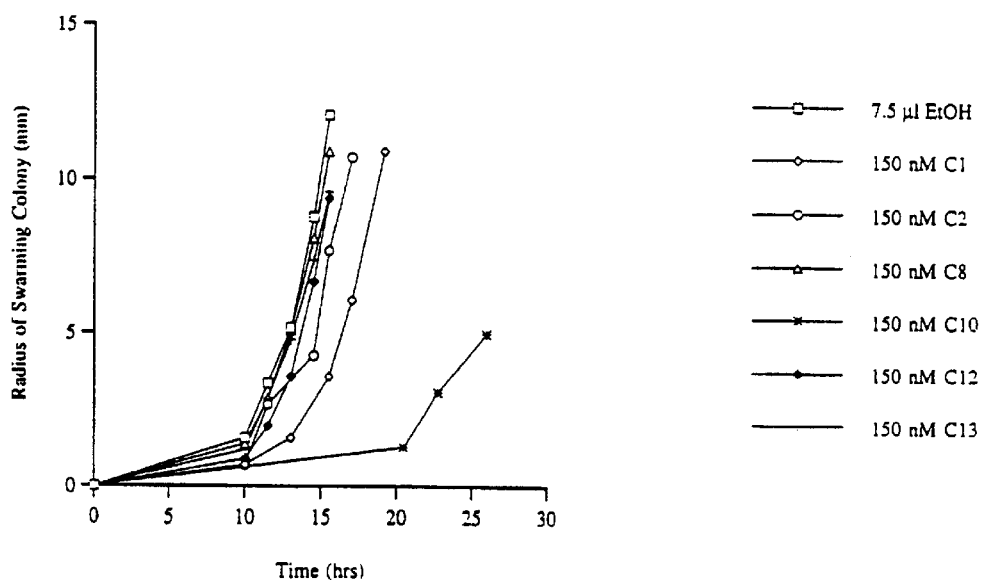

The effects of furanones on AHL dependent phenotypes, and growth, for the AHL assay strains number of bacterial species are shown in Table 1. In all instances some of the furanones affected AHL dependent phenotypes at concentrations that did not inhibit growth. The most complete set of results was obtained for Serratia liquefaciens, a facultative plant pathogen. None of the furanones tested inhibited growth or swimming behaviour of this organism. All compounds tested, however, inhibited swarming, a AHL dependent behaviour, to varying degrees (FIGS. 4a, 4b and Table 1). This demonstrates the presence of a mechanism that interferes with bacterial cell to cell communication and thereby limits bacterial surface colonisation without affecting growth or survival of the bacteria. In an analogous fashion, compounds 3 and 4 inhibit production of exoproteases by Serratia exoproteases at concentrations where growth is unaffected (none of the compounds tested inhibited growth of Serratia liquefaciens at 100 μg/ml).

Indigo formation in Chromobacterium violencia, an HSL regulated system, is inhibited by compounds 1 and 2 (Table 2). These two compounds have no effect on the growth of this bacterium. The indigo negative Chromobacterium violencia mutant did not produce the pigment in response to the addition of compounds 1 and 2 (e.g. the compounds do not stimulate indigo production). As for Serratia, the compounds appear to specifically interfere with an AHL mediated process, rather than having gross effects (e.g. inhibition of growth) on the organism. In both cases, the results suggest competitive inhibition of HSLs by the compounds of the invention. Growth of Chromobacterium was inhibited by 100 ug/ml of compound 4 but unaffected by the same concentration of compounds 1–3.

The compounds also affect AHL mediated processes in two important pathogens, the human pathogen Pseudomonas aeruginosa (cystic fibrosis) and the plant pathogen Erwinia carotovora (soft rot disease). Production of elastase, which is an AHL mediated virulence factor for P. aeruginosa, is stimulated by compounds 1 and 2, but inhibited by compounds 3 and 4. There is no detectable effect of compounds 2 and 4 on growth. The observation that structurally very similar compounds (1 and 2 versus 3 and 4) can have opposite effects on elastase production again indicates a very specific effect of the compounds on this HSL mediated system.

For Erwinia carotovora, compound 4 decreases exoenzyme production without inhibiting growth. Compound 3 has no effect on either growth or exoenzyme formation, again supportive of the specific effects of these metabolites.

Furanones inhibit AHL regulated bioluminescence in both Vibrio fischeri and V. harveyi without inhibiting growth of either strain (Table 2).

TABLE 1

Effect of furanone compounds on bacterial species with acylated homoserine lactone phenotypes

| Organism | | Serratia liquefacions | Chromobacterium violencia | Vibrio fisheri | Vibrio harveyi | Psoudomonas aeruginosa | Erwinia carotovora |
|---|---|---|---|---|---|---|---|
| Significance | | plant pathogen | | marine symbiont | marine symbiont | opportunistic human pathogen cystic fibrosis | plant (potato) pathogen |
| HSL phenotype | | swarming   exoenzymes | indigo formation | luminescence | luminescence | elastase       Exoloxin A | exoenzymes |
| acryl-HSL type | | HB-HSL | | OH-HSL a.o. | HB-HSL | ODD-HSL | OH-HSL |
| Effect of | 1 | no effect | no effect | no effect | no effect | nt | nt |
| Furanone | 2 | no effect | no effect | no effect | no effect | nt | nt |
| compounds 1–4 on | 3 | no effect | slowed | no effect | no effect | no effect | no effect |
| bacterial growth | 4 | no effect | inhibit | no effect | no effect | no effect | no effect |
| Effect of | 1 | inhibit       nt | inhibit | inhibit | inhibit | stimulated        nt | nt |
| Furanone | 2 | inhibit       nt | inhibit | inhibit | inhibit | stimulated        nt | nt |
| compounds 1–4 on | 3 | inhibit       decrease/inhibit | nt | inhibit | inhibit | delay/inhibited       nt | no effect |
| HSL phenotype | 4 | inhibit       decrease/inhibit | nt | inhibit | inhibit | delay/inhibited       nt | inhibit |
| Comments | | *Growth and swimming is not inhibited by 100 µg/ml of either compound. *100 µg/ml of 3 and 4 decreases the exoprotease activity of the wild type and eliminates the exoprotease activity of the mutant | *Growth inhibited by 4 and slowed by 3 (each 100 µg/ml | *All compounds inhibitory at 100 µg/ml. 4 most inhibitory V. fisheri more sensitive than V. harveyi *No visible effect on luminescence of lower concentrations (based on visual inspection of agar plates | | *Growth on plates unaffected by 100 µg/ml of either compound *Elastase production is also highly media dependant | |

HB: N-(3-hydroxybutanyl); OH: N-(3-oxhexanyl); OO: N-(3-oxyocytanoyl); ODD: N-(3-oxydodecanyl) nt = not tested

TABLE 2

Minimum inhibitory concentrations of *Delisea pulchra* crude extract and furanone compounds inhibitory to four fouling relevant phenotypes: swimming, attachment, growth and swarming in strains isolated from *D. pulchra* and rock surfaces.

| | | Concentration of D. pulchra crude extract (DC) or furanone compound (1–4) inhibiting four phenotypes | | | |
|---|---|---|---|---|---|
| Strain | Compound | Swimming (µg/ml) | Attachment (µg/cm²) | Growth(2) (µg/ml) | Swarming (µg/ml) |
| R12 | DC | nd(1) | 0.01 | nd | nd |
| | D1 | >50 | nd | >50 | 5 |
| | D2 | >50 | nd | >50 | 5 |
| | D3 | 50 | nd | >50 | 5 |
| | D4 | 25 | nd | 25 | 5 |
| R86 | DC | nd | 0.01 | nd | nd |
| | D1 | 50 | nd | >50 | 25 |
| | D2 | >50 | nd | >50 | 5 |
| | D3 | >50 | nd | >50 | 5 |
| | D4 | 25 | nd | 25 | 5 |
| R130 | DC | nd | 0.01 | nd | nd |
| | D1 | >50 | nd | >50 | 25 |
| | D2 | >50 | nd | >50 | 25 |
| | D3 | >50 | nd | 25 | 25 |
| | D4 | 25 | nd | 25 | 5 |
| V21 | DC | nd | 1.0 | nd | nd |
| | D1 | 25 | nd | 25 | 5 |
| | D2 | 25 | nd | 25 | 5 |
| | D3 | 25 | nd | 5 | 5 |
| | D4 | 5 | nd | 5 | 5 |
| V54 | DC | nd | 1.0 | nd | nd |
| | D1 | 5 | nd | >50 | 25 |
| | D2 | 5 | nd | >50 | 5 |
| | D3 | 5 | nd | 25 | 5 |
| | D4 | 5 | nd | 25 | 5 |
| V55 | DC | nd | 1.0 | nd | nd |
| | D1 | 5 | nd | >50 | 5 |
| | D2 | 5 | nd | >50 | 5 |
| | D3 | 5 | nd | 5 | 5 |
| | D4 | 5 | nd | 25 | 5 |

(1) not done
(2) in liquid media

Inhibition of Surface Motility and Adhesion

Figure 5A:
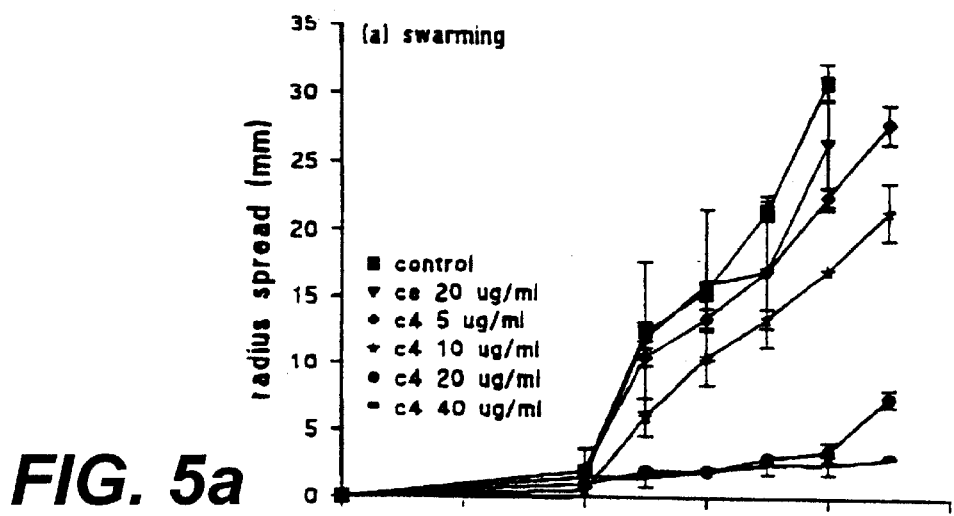
FIG. 5 shows the effect of furanone compound 4 on (a) swarming LB10 with 1.5% agar, (b) swimming LB10 with 0.3% agar, and (c) growth of *Proteus mirabilus* at 37 C.
Figure 5B:
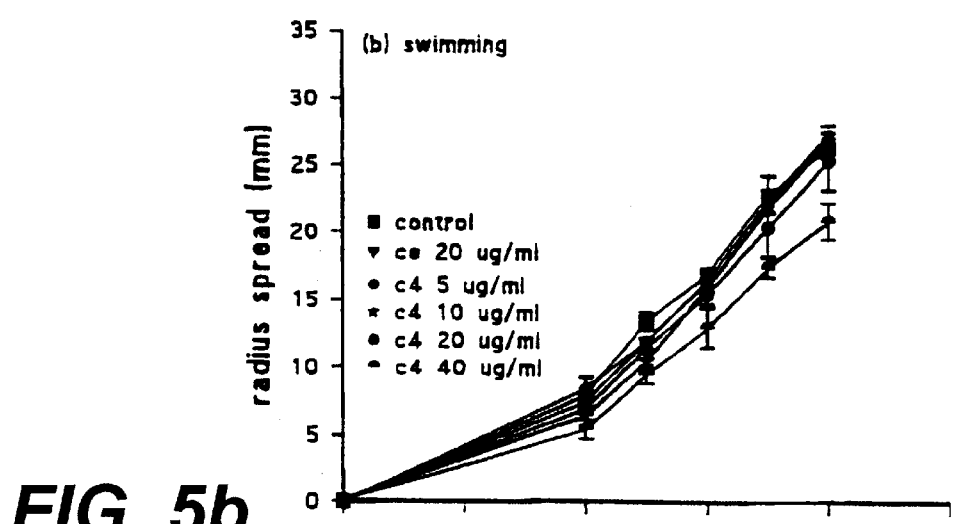
Figure 5C:
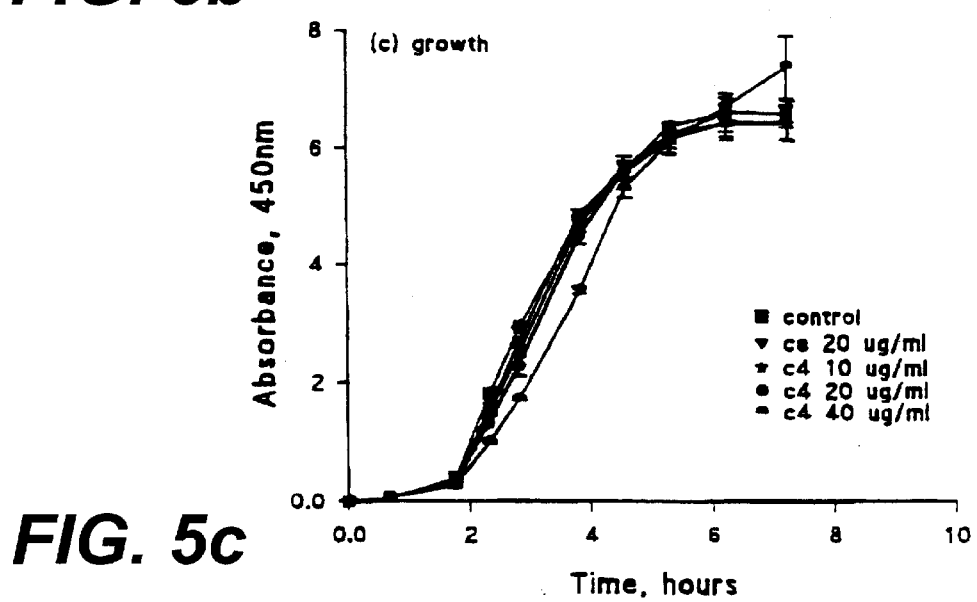

Both crude extract of Delisea, and compound 4, inhibited swarming by the opportunistic human pathogen *Proteus mirabilis*. Compound 4 did not affect growth or swimming at concentrations that were inhibitory to swarming (FIG. 5). Swarming of all 6 marine strains was also inhibited by furanones at concentrations that did not inhibit growth (Table 2).

Figure 6A:
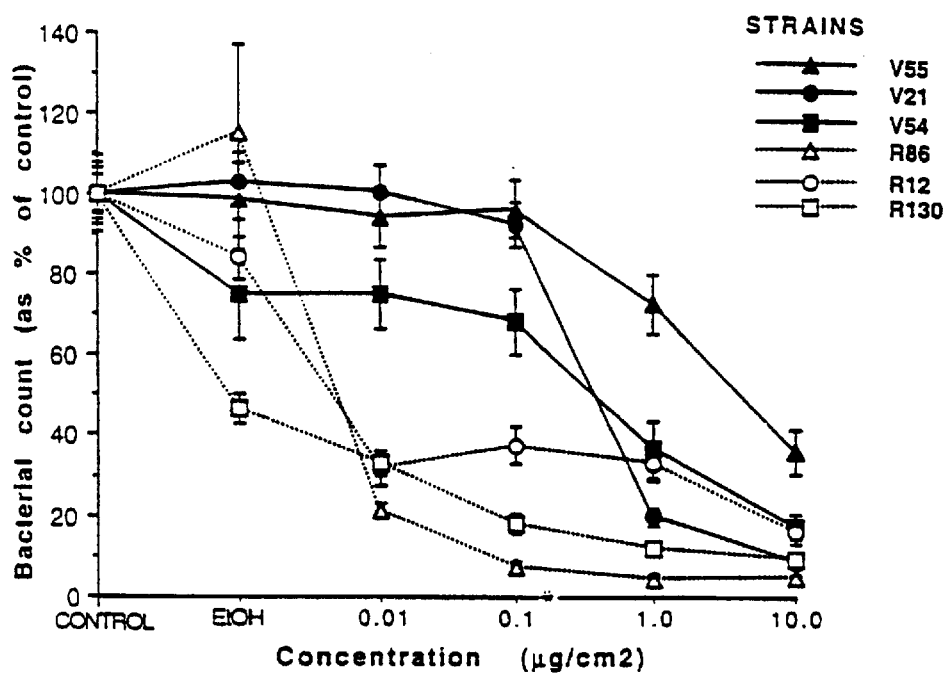
FIG. 6 shows the effects of crude extracts of Delisea when coated on plastic against (a) six strains of bacteria in the laboratory and (b) attachment of bacteria in the field.
Figure 6B:
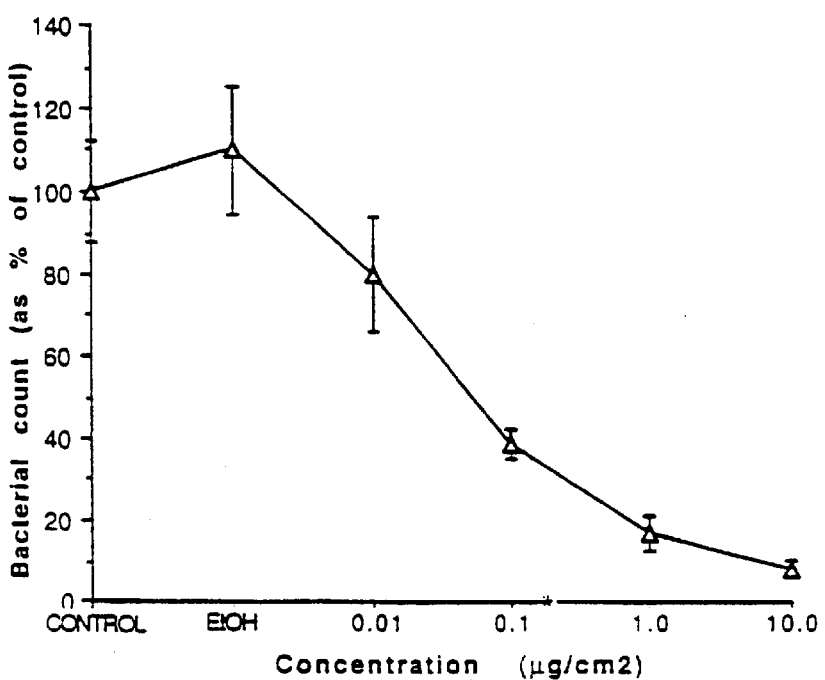

When the crude non-polar extract of Delisea was coated onto artificial surfaces in laboratory assays it inhibited adhesion by all six marine isolates tested. Inhibition of some strains occurred at concentrations as low as 10 ng/cm²; 5 of 6 strains were inhibited by 1 ug/cm² (FIG. 6A). Results of field assays of bacterial adhesion were consistent with these results. Crude Delisea extract coated onto surfaces at 1 ug/cm$^2$ decreased bacterial adhesion by >90% in the field (FIG. 6B).

Pre-incubation of bacteria with crude non-polar extract of Delisea, followed by washing of the cells, also significantly inhibited subsequent adhesion of the bacteria to (uncoated) inanimate surfaces. This result is particularly telling with regard to the results for inhibition of AHL regulatory systems described above. This is because the pre-incubation experiments demonstrate that the furanones are not simply inhibiting adhesion by changing surface characteristics. Rather they are taken up by the cells, with the result that adhesion is then inhibited, and indicating that a regulatory system has been affected resulting in a loss of production of adhesin[s]. Further evidence that the regulatory system affected is AHL driven comes from the observation (data not shown) that when cells are pre-incubated with AHLs, adhesion increases. Although many adhesion assays were done with crude extract of Delisea, it will be appreciated by one skilled in the art that the effects are due to the furanones which are contained within the extract.

Inhibition of Fungal Growth by Compounds of Formula 2

All compounds inhibited either *Candida albicans* or Helminthosporium sp. for at least one of the levels tested (Table 3). The compounds were most effective against Helminthosporium, with activities in some cases comparable to that of the commercial fungicide Amphotericin B. At the highest levels tested, growth of Helminthosporium was completely inhibited by 4 of the furanones: unlike the effects of Amphotericin B. It is also emphasised that these assays underestimate the effects of these compounds relative to the commercial product, since diffusion of these compounds through agar is much less than that of the water soluble amphotericin B.

These results clearly demonstrate that natural furanones and synthetic analogues:

(i) Specifically interfere with bacterial properties that are regulated by homoserine lactone or acylated homoserine lactone regulatory systems. Specific properties known to be regulated by AHLs shown to be affected here include swarming, exoenzyme production, bioluminescence, and pigment production. Adhesion, which is stimulated by the addition of AHLs and is also likely to be AHL regulated, was also inhibited by the furanones tested. Similarly, swarming of *Proteus mirabilis* and a number marine isolates, was also inhibited by the furanones. It should be noted that other AHL regulated processes or properties not tested here are also likely to be inhibited by furanones including virulence in the fish pathogen *Vibrio anguillarum*, plasmid transfer in *Agrobacterium tumefaciens*.

(ii) Some of the compounds (formula 2) tested also inhibit growth and or kill both bacteria and fungi.

TABLE 3

Inhibition of fungal growth by furanones. Data are width (mm) of inhibition zone.

| Compound | Amount Added (µg) | | | |
|---|---|---|---|---|
| | 100 | 10 | 1 | 0.1 |
| *Candida albicans* | | | | |
| Control | no inhibition | | | |
| Ethanol | no inhibition | | | |

TABLE 3-continued

Inhibition of fungal growth by furanones. Data are width (mm) of inhibition zone.

| Compound | Amount Added (µg) | | | |
|---|---|---|---|---|
| | 100 | 10 | 1 | 0.1 |
| Amphotericin B | 1.14 | 6–10 | 5–7 | 2–4 |
| Compound 1 | 1–2 | 0 | 0 | 0 |
| Compound 2 | 2–3 | 0 | 0 | 0 |
| Compound 3 | 2–3 | 1–2 | 0 | 0 |
| Compound 5 | 3–8 | 1 | 0 | 0 |
| Compound 8 | 0 | 0 | 0 | 0 |
| Compound 13 | 1 | 0 | 0 | 0 |
| Helminthosporium sp | | | | |
| Control | no inhibition | | | |
| Ethanol | no inhibition | | | |
| Amphotericin B | 7–10 | 6–8 | 6 | 2 |
| Compound 1 | 20 | 2–5 | 0 | 0 |
| Compound 2 | 20 | 2–4 | 0 | 0 |
| Compound 3 | 6–20 | 6–9 | 0 | 0 |
| Compound 5 | 20 | 9–13 | 2–4 | 0 |
| Compound 8 | 20 | 0 | 0 | 0 |
| Compound 13 | 0 | 0 | 0 | 0 |

Thus these compounds, taken as a whole, can interfere with AHL driven systems in microorganisms as well as inhibit growth of some strains. The effects are highly specific and are dependent on concentration of the furanone compounds, on the strain tested and on the structure of the furanones and on the given AHL mediated system. Furanones can be used to specifically inhibit HSL systems without inhibiting growth, as well as being used to inhibit growth. Because of the widespread occurrence of HSL mediated functions in bacteria, furanones in this context may be useful in many applications, including but not restricted to biomedical, agricultural, and antifouling applications.

It is noted that some previous work on the activity of some of these compounds as biocidal agents has been done, in particular the results reported by Reichelt and Borowitzka (1984). Their results show that several of the furanones of Formula 1 inhibited growth of bacteria, however, there is no indication or teaching that furanones can effect specific regulatory systems. The present inventors have found that furanones strongly inhibit specific properties (exoenzyme production, swarming, etc.) of these bacteria and these compounds can be used in a variety of in vitro and in vivo systems to effect such properties.

It will be appreciated by persons skilled in the art that numerous variations and/or modifications may be made to the invention as shown in the specific embodiments without departing from the spirit or scope of the invention as broadly described. The present embodiments are, therefore, to be considered in all aspects as illustrative and not restrictive.

References de Nys, R., Coll, J. C., Bowden, B.F. (1992). *Delisea pulchra* (cf. fimbriata) revisited. Ths structural determination of two new metabolies from the red alga *Delisea pulchra*. *Aus. J. Chem.* 45: 1625–1632.

de Nys, R., Wright, A. D., Konig, G. M., Sticher, O. (1993). New halogenated furanones from the marine alga *Delisea pulchra* (cf. fimbriata). *Tetrahedron* 49: 11213–11220.

Flethcer, R. L. (1989). A bioassay technique using the marine fouling green ala Enteromorpha. *Int. Biodeterioriation* 25: 407–422.

Fuqua, W. C., Winans, S. C., Greenberg, E. P. (1991) Quorum sensing in bacteria: the LuxR-LuxI family of cell density-responsive transcriptional regulators. *J. Bacteriology* 176: 269–275.

Jefford, C. W., Jaggi, D., Boukouvalas, J. (1988). *J. Chem, Soc., Chem. Comm.*: 1595.

Jefford, C. W., Jaggi, D., Sledeski, A. W. Boukouvalas, J. (1989) *Stud. Nat. Prod. Chem.*, 3: 157.

Kazlauskas, R., Murphy, P. T., Quinn, R. J., Wells, R. J. (1977). A new class of halogenated lactones from the red alga *Delisea fimbriata* (Bonnemaisoniaceae). *Tet. Lett.* 1: 37–40.

Reichelt, J. L., Borowitzka, M. A. (1984) Antimicrobial activity from marine algae; results of a large scale screening programme. *Hydrobiologia* 116/117:158–168.

Swift, S., Bainton, N. J. Winson, M. K. (1994). Gram-negative bacterial communication by N-acyl homoserine lactones: a universal language? *Trends in Microbiology* 2: 193–198.

What is claimed is:

1. A method of inhibiting an homoserine lactone and/or acylated homoserine lactone regulated process in a microorganism, the method comprising exposing a microorganism having an homoserine lactone and/or acylated homoserine lactone regulated process to an amount of a furanone compound having Formula 1 effective to inhibit the process but not to inhibit the growth of the microorganism,

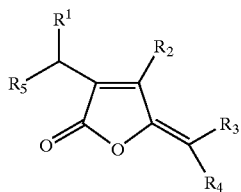

Formula 1 wherein: $R_1$ is a hydrogen, hydroxyl, acetoxy, ester or ether group; $R_2$ is Br or H; $R_3$ and $R_4$ are independently selected from the group consisting of a hydrogen atom and a halogen atom; and $R_5$ is selected from the group consisting of $C_1$, $C_3$, $C_5$ and $C_{11}$ alkyl.

2. The method according to claim 1 wherein the homoserine lactone and/or acylated homoserine lactone regulated process is selected from the group consisting of motility, swarming, swimming, exoenzyme production, indigo formation, luminescence, adhesion and attachment.

3. The method according to claim 2 wherein the homoserine lactone and/or acylated homoserine lactone regulated process is motility or swarming and the furanone compound is incorporated in a microbial culture medium at a concentration greater than 10 ng/ml so as to inhibit motility or swarming of the microorganism.

4. The method according to claim 3 wherein the furanone compound is incorporated in the culture medium at a concentration from 1 μg to 100 μg/ml.

5. The method according to claim 2 wherein the homoserine lactone and/or acylated homoserine lactone regulated process is adhesion or attachment and the furanone compound is applied to a surface at a concentration greater than 1 ng/cm² so as to inhibit adhesion or attachment of the microorganism to the surface.

6. The method according to claim 5 wherein the furanone compound is applied to the surface at a concentration from 10 ng to 10 μg/cm².

7. The method according to claim 1 wherein the furanone compound is used at a concentration greater than 10 ng/ml.

8. The method according to claim 7 wherein the furanone compound is used at a concentration from 100 ng to 1 mg/ml.

9. The method according to claim 8 wherein the furanone compound is used at a concentration from 1 μg to 100 μg/ml.

10. The method according to claim 1 wherein the microorganism is a pathogen of plant, crustacean, fish, animal or human.

11. The method according to claim 10 wherein the plant pathogen is selected from the group consisting of *Serratia liquefaciens* and *Erwinia carotovora*.

12. The method according to claim 10 wherein the crustacean pathogen is *Vibrio harveyi*.

13. The method according to claim 10 wherein the fish pathogen is *Vibrio anguillarum*.

14. The method according to claim 10 wherein the human pathogen is selected from the group consisting of *Pseudomonas aeruginosa* and *Proteus mirabilis*.

15. A method of inhibiting an homoserine lactone and/or acylated homoserine lactone regulated process in a microorganism, the method comprising exposing a microorganism having an homoserine lactone and/or acylated homoserine lactone regulated process to an amount of a furanone compound having Formula 2 effective to inhibit the process but not to inhibit the growth of the microorganism,

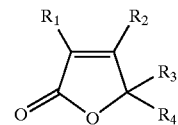

Formula 2 wherein:

$R_1$, $R_2$, $R_3$ and $R_4$ are each independently selected from the group consisting of a hydrogen, halogen, hydroxyl, methyl, alkyl, ether and ester group.

16. The method according to claim 15 wherein the homoserine lactone and/or acylated homoserine lactone regulated process is selected from the group consisting of motility, swarming, swimming, exoenzyme production, indigo formation, luminescence, adhesion and attachment.

17. The method according to claim 16 wherein the homoserine lactone and/or acylated homoserine lactone regulated process is motility or swarming and the furanone compound is incorporated in a microbial culture medium at a concentration greater than 10 ng/ml so as to inhibit motility or swarming of the microorganism.

18. The method according to claim 17 wherein the furanone compound is incorporated in the culture medium at a concentration from 1 μg to 100 μg/ml.

19. The method according to claim 16 wherein the homoserine lactone and/or acylated homoserine lactone regulated process is adhesion or attachment and the furanone compound is applied to a surface at a concentration greater than 1 ng/cm² so as to inhibit adhesion or attachment of the microorganism to the surface.

20. The method according to claim 19 wherein the furanone compound is applied to the surface at a concentration from 10 ng to 10 μg/cm².

21. The method according to claim 15 wherein the furanone compound is used at a concentration greater than 10 ng/ml.

22. The method according to claim 21 wherein the furanone compound is used at a concentration from 100 ng to 1 mg/ml.

23. The method according to claim 22 wherein the furanone compound is used at a concentration from 1 μg to 100 μg/ml.

24. The method according to claim 15 wherein the microorganism is a pathogen of plant, crustacean, fish, animal or human.

25. The method according to claim 24 wherein the plant pathogen is selected from the group consisting of *Serratia liquefaciens* and *Erwinia carotovora*.

26. The method according to claim 24 wherein the crustacean pathogen is *Vibrio harveyi*.

27. The method according to claim 24 wherein the fish pathogen is *Vibrio anguillarum*.

28. The method according to claim 24 wherein the human pathogen is selected from the group consisting of *Pseudomonas aeruginosa* and *Proteus mirabilis*.

29. A method of inhibiting an homoserine lactone and/or acylated homoserine lactone regulated process in a microorganism, the method comprising exposing a microorganism having an homoserine lactone and/or acylated homoserine lactone regulated process to an amount of a furanone compound having Formula 1 effective to inhibit the process but not to inhibit the growth of the microorganism,

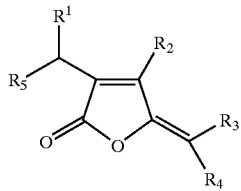

Formula 1 wherein:
compound 1 has R1=H, R2=Br, R3=Br, R4=Br, and R5=$C_3$ alkyl;
compound 2 has R1=H, R2=Br, R3=H, R4=Br, and R5=$C_3$ alkyl;
compound 3 has R1=OAc, R2=Br, R3=H, R4=Br, and R5=$C_3$ alkyl;
compound 4 has R1=OH, R2=Br, R3=H, R4=Br, and R5=$C_3$ alkyl;
compound 5 has R1=OAc, R2=Br, R3=H, R4=I, and R5=$C_3$ alkyl;
compound 8 has R1=H, R2=H, R3=Br, R4=Br, and R5=$C_3$ alkyl;
compound 10 has R1=OAc, R2=Br, R3=Br, R4=Br, and R5=$C_3$ alkyl;
compound 15 has R1=H, R2=Br, R3=Br, R4=Br, and R5=$C_1$ alkyl;
compound 16 has R1=H, R2=Br, R3=H, R4=Br, and R5=$C_1$ alkyl;
compound 17 has R1=H, R2=H, R3=Br, R4=Br, and R5=$C_1$ alkyl;
compound 12 has R1=H, R2=Br, R3=H, R4=Br, and R5=$C_5$ alkyl;
compound 13 has R1=H, R2=H, R3=Br, R4=Br, and R5=$C_5$ alkyl; and
compound 14 has R1=H, R2=H, R3=Br, R4=Br, and R5=$C_{11}$ alkyl.

30. The method according to claim 29 wherein the homoserine lactone and/or acylated homoserine lactone regulated process is selected from the group consisting of motility, swarming, swimming, exoenzyme production, indigo formation, luminescence, adhesion and attachment.

31. The method according to claim 30 wherein the homoserine lactone and/or acylated homoserine lactone regulated process is motility or swarming and the furanone compound is incorporated in a microbial culture medium at a concentration greater than 10 ng/ml so as to inhibit motility or swarming of the microorganism.

32. The method according to claim 31 wherein the furanone compound is incorporated in the culture medium at a concentration from 1 µg to 100 µg/ml.

33. The method according to claim 30 wherein the homoserine lactone and/or acylated homoserine lactone regulated process is adhesion or attachment and the furanone compound is applied to a surface at a concentration greater than 1 ng/cm² so as to inhibit adhesion or attachment of the microorganism to the surface.

34. The method according to claim 33 wherein the furanone compound is applied to the surface at a concentration from 10 ng to 10 µg/cm².

35. The method according to claim 29 wherein the furanone compound is used at a concentration greater than 10 ng/ml.

36. The method according to claim 35 wherein the furanone compound is used at a concentration from 100 ng to 1 mg/ml.

37. The method according to claim 36 wherein the furanone compound is used at a concentration from 1 µg to 100 µg/ml.

38. The method according to claim 29 wherein the microorganism is a pathogen of plant, crustacean, fish, animal or human.

39. The method according to claim 38 wherein the plant pathogen is selected from the group consisting of *Serratia liquefaciens* and *Erwinia carotovora*.

40. The method according to claim 38 wherein the crustacean pathogen is *Vibrio harveyi*.

41. The method according to claim 38 wherein the fish pathogen is *Vibrio anguillarum*.

42. The method according to claim 38 wherein the human pathogen is selected from the group consisting of *Pseudomonas aeruginosa* and *Proteus mirabilis*.

* * * * *